US00PP36315P2

(12) United States Plant Patent
Oudshoorn

(10) Patent No.: US PP36,315 P2
(45) Date of Patent: Dec. 10, 2024

(54) ***PAPAVER* PLANT NAMED 'HG01'**

(50) Latin Name: *Papaver orientale*
Varietal Denomination: HG01

(71) Applicant: Herbert Oudshoorn, Rijpwetering (NL)

(72) Inventor: Herbert Oudshoorn, Rijpwetering (NL)

( * ) Notice: Subject to any disclaimer, the term of this patent is extended or adjusted under 35 U.S.C. 154(b) by 0 days.

(21) Appl. No.: 18/236,878

(22) Filed: Aug. 22, 2023

(51) Int. Cl.
*A01H 5/02* (2018.01)
*A01H 6/64* (2018.01)

(52) U.S. Cl.
USPC ..... Plt./464
CPC ..... *A01H 6/64* (2018.05)

(58) Field of Classification Search
USPC ..... Plt./464
CPC ..... A01H 6/64; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Papaver* plant named 'HG01' is disclosed, characterized by large, red flowers with short, strong stems, and leaves that stay green while flowering. Plants are compact, and disease-resistant. The new variety is a *Papaver,* normally produced as a cut flower and potentially useful as an ornamental plant.

3 Drawing Sheets

Latin name of the genus and species: *Papaver orientale.*
Variety denomination: 'HG01'.

BACKGROUND OF THE INVENTION

The new *Papaver* cultivar is a product of a planned breeding program conducted by the inventor to produce new, healthy varieties with strong stems, and high disease resistance. The cross resulting in this new variety was made during 2016 at a nursery in Heerhugowaard, the Netherlands.

The seed parent is an unpatented, unnamed *Papaver orientale* of the inventor's own breeding. The pollen parent is the unpatented *Papaver* 'Patty's Plum'. The new variety was selected in 2018 by the inventor at the same nursery in Heerhugowaard, the Netherlands.

Asexual reproduction of the new cultivar was first performed by tissue culture in 2019 in Heerhugowaard, the Netherlands. Subsequent propagation has shown that the unique features of this cultivar are stable and reproduced true to type in multiple successive generations.

SUMMARY OF THE INVENTION

The cultivar 'HG01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'HG01'. These characteristics in combination distinguish 'HG01' as a new and distinct *Papaver* cultivar:

1. Large red flowers.
2. Short flower stems, making a more compact plant.
3. Strong flower stems.
4. Healthy green foliage that stays green when flowering.

5. Sturdy, hairy leaves.
6. High resistance to *Botrytis.*

PARENT COMPARISONS

Plants of the new cultivar 'HG01' are similar to plants of the seed parent, in most horticultural characteristics, however, plants of the new cultivar 'HG01' differ in the following;

1. Flower color of the new variety is red, while the flower color of the seed parent is pink.

Plants of the new cultivar 'HG01' are similar to plants of the pollen parent, in most horticultural characteristics, however, plants of the new cultivar 'HG01' differ in the following;

1. Flower color of the new variety is red, while the flower color of the pollen parent is pale pink-purple.
2. The new variety is a more compact plant than the pollen parent.
3. The new variety is more disease-resistant than the pollen parent.

COMMERCIAL COMPARISONS

Plants of the new cultivar 'HG01' are comparable to the unpatented commercial variety *Papaver* 'Goliath'. The two *Papaver* varieties are similar in most horticultural characteristics; however, the new variety 'HG01' differs in the following:

1. Plants of the new variety are not as tall as this comparator.

Plants of the new cultivar 'HG01' are comparable to the unpatented common *Papaver orientale.* The two *Papaver* varieties are similar in most horticultural characteristics; however, the new variety 'HG01' differs in the following:

1. The new variety is more disease-resistant than this comparator.

2. Foliage of the new variety remains green while flowering, while foliage of this comparator turns yellow while flowering.
3. The new variety is a more compact plant than this comparator.

BRIEF DESCRIPTION OF THE PHOTOGRAPHS

The accompanying photograph in FIG. 1 illustrates in full color a typical flowering plant of the new variety at approximately 7 months old, grown outdoors during the spring in Waddinxveen, the Netherlands.

Figure 1:
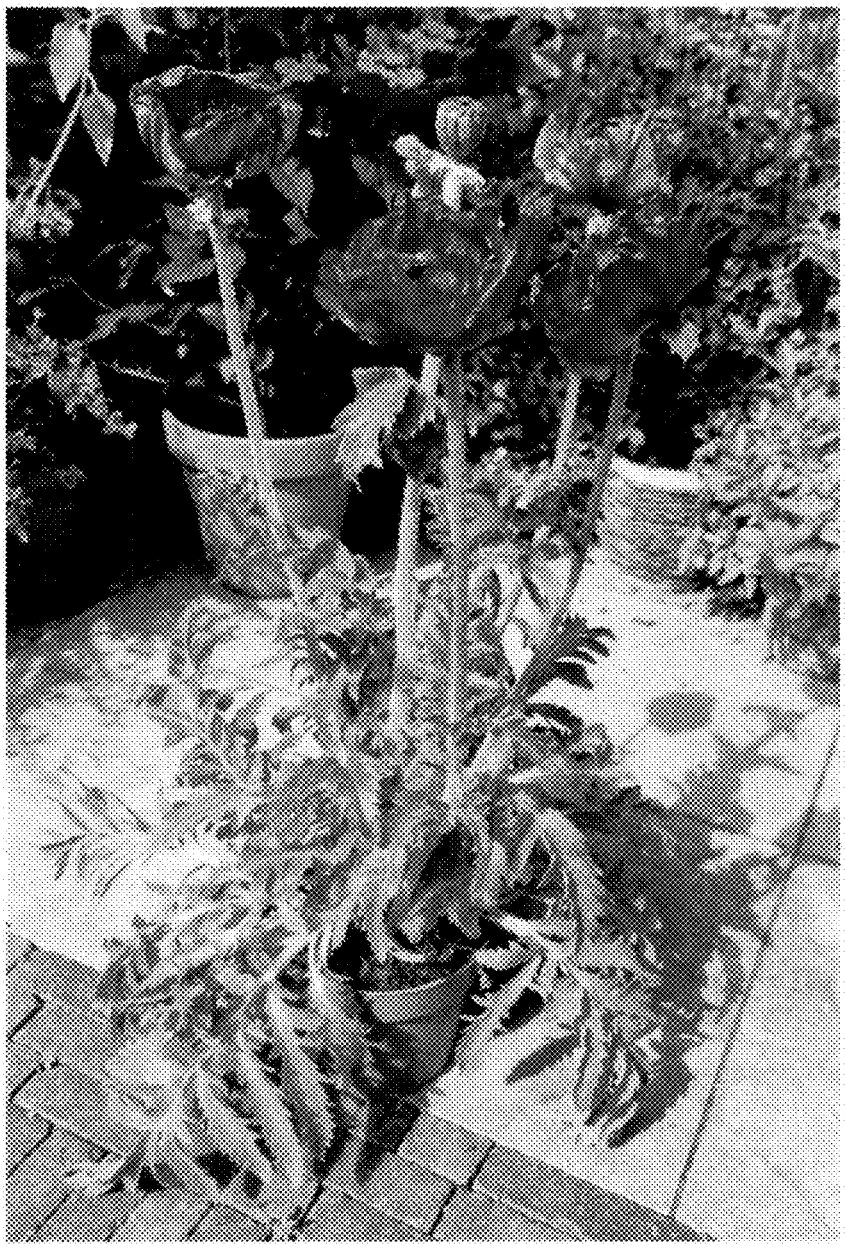
Figure 2:
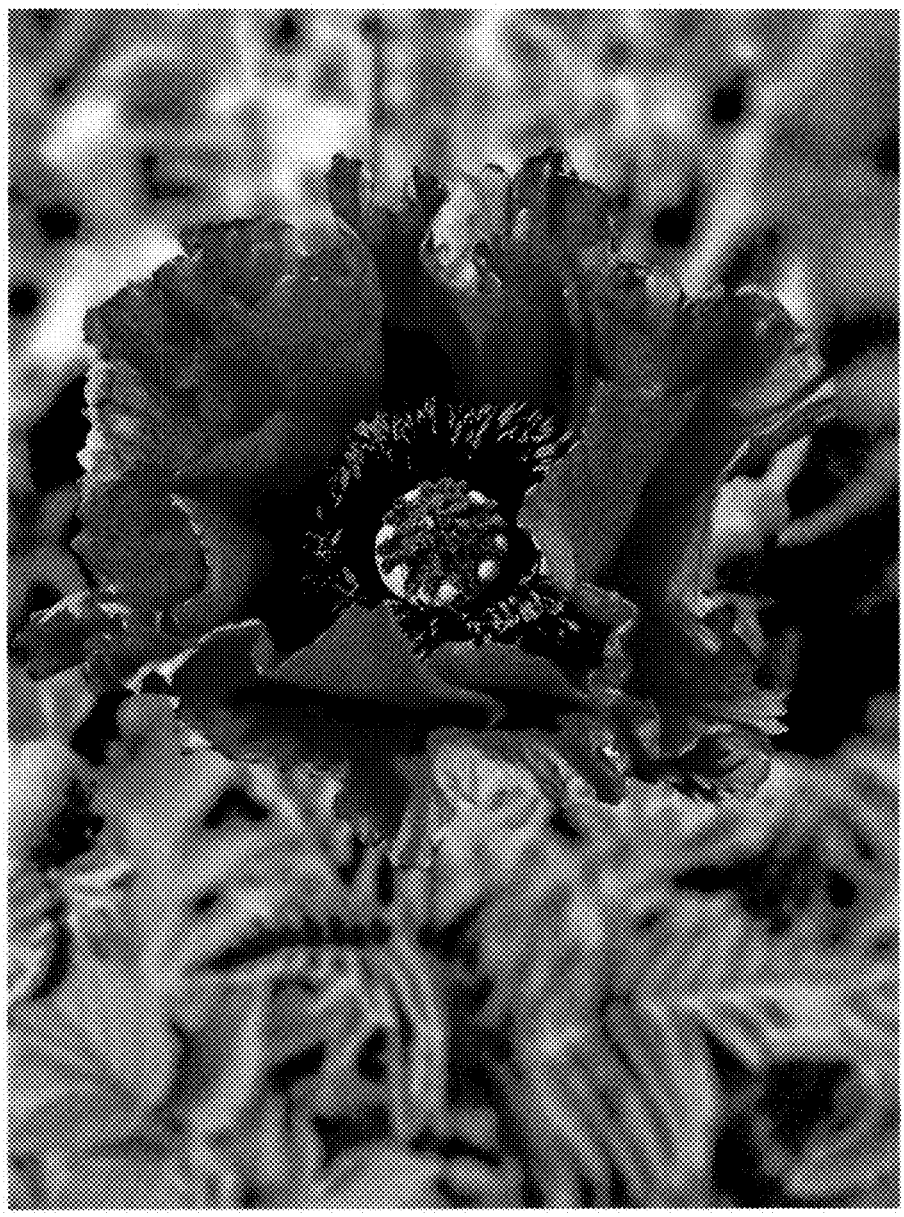
FIG. 2 illustrates a close-up view of the flower.
Figure 3:
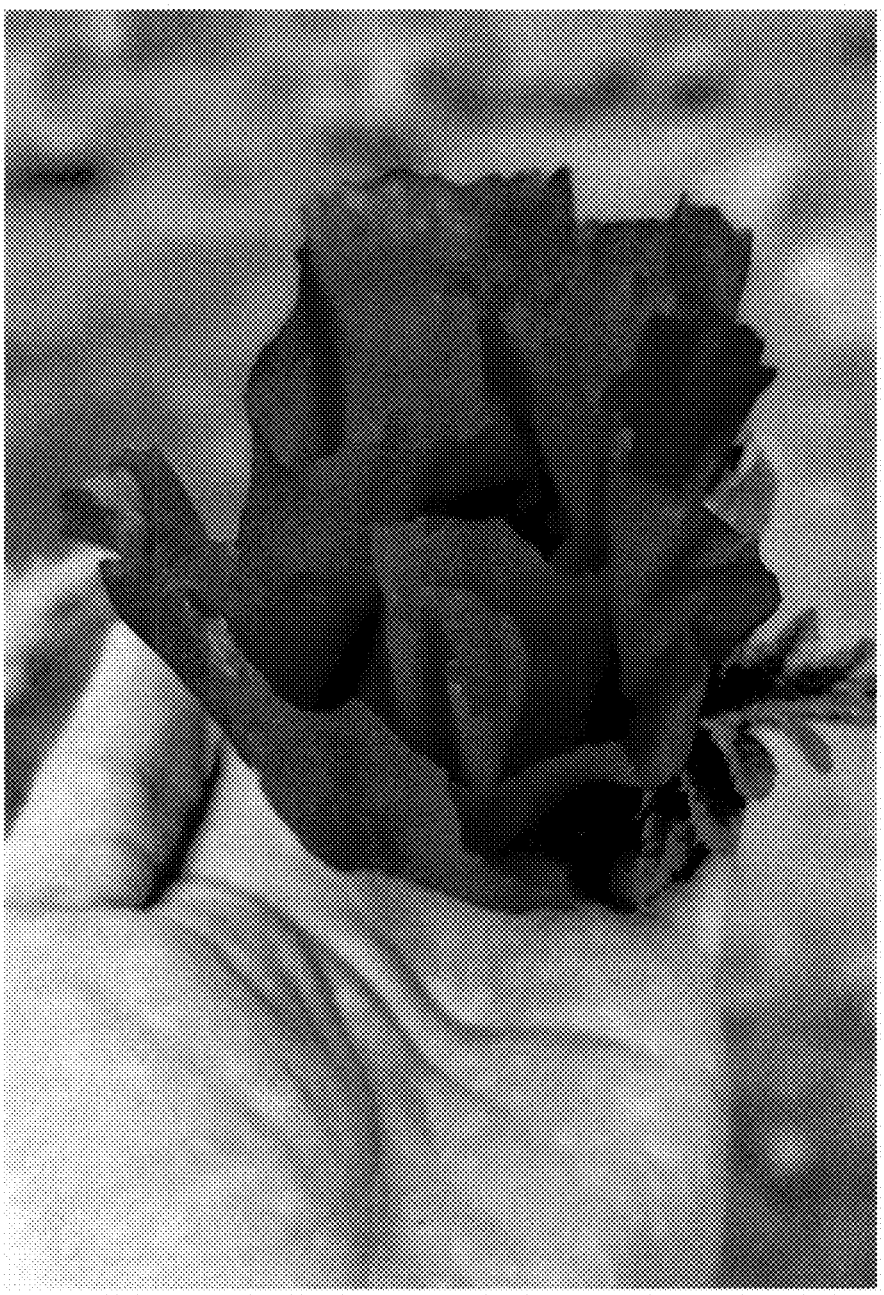
FIG. 3 illustrates a flower beginning to open; the strong red color of the under petal can be seen.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 6$^{th}$ edition, except where general terms of ordinary dictionary significance are used. The following observations and measurements describe 7-month-old 'HG01' plants grown outdoors in Waddinxveen, the Netherlands. The growing temperature ranged from 12° C. to 26° C. during the day and from 0° C. to 6° C. during the night. General light conditions are bright, normal sunlight. Measurements and numerical values represent averages of typical plant types.

Botanical classification: *Papaver orientale* 'HG01'.

PROPAGATION

Time to rooting: 6 to 8 weeks.
Time to produce a rooted plant: 6 weeks.
Root description: Thick, light brown in color, not accurately measured using R.H.S. chart.

PLANT

Plant type: Herbaceous perennial.
Growth habit: Upright.
Height: 38 cm.
Spread: 52 cm.
Growth rate: Vigorous.
Branching habit: Basal.

FOLIAGE

Leaf:
- *Arrangement*.—Alternate.
- *Length*.—22 cm.
- *Width*.—17 cm.
- *Shape*.—Lanceolate, deeply dissected.
- *Apex*.—Pinnatifid.
- *Base*.—Cuneate.
- *Margin*.—Serrate, occasionally bi-serrate.
- *Texture*.—Pubescent, rough.
- *Color*.—Young Foliage Upper Side: RHS Yellow-Green 144A. Young Foliage Under Side: RHS Green 137C. Mature Foliage Upper Side: RHS Green NN137A and 137B. Mature Foliage Under Side: RHS Green 137C.
- *Venation*.—Type: Pinnate. Color, Upper Side: Near RHS Yellow-Green 145C Color, Under Side: Near RHS Yellow-Green 145C
- *Petiole*.—Length: 7 cm. Diameter: 1 cm. Color: RHS Yellow-Green 144C and 144D.

FLOWER

Bud:
- *Shape*.—Ovate.
- *Length*.—4 cm.
- *Diameter*.—2.8 cm.
- *Color*.—RHS Green 137B.
- *Texture*.—Pubescent, rough.

Flower:
- *Blooming period*.—May to June.
- *Type*.—Single, terminal.
- *Height*.—5.5 cm.
- *Diameter*.—16 cm.
- *Longevity*.—About 3 days.
- *Persistence*.—Self-Cleaning.
- *Fragrance*.—None.

Petals:
- *Arrangement*.—Rotate.
- *Quantity*.—4 per flower.
- *Length*.—8 cm.
- *Width*.—9.2 cm.
- *Texture*.—Smooth.
- *Apex*.—Broadly obtuse.
- *Shape*.—Irregular orbicular.
- *Margin*.—Wavy, with small incisions.
- *Color*.—Immature Upper Surface: Near RHS Red 46A with Red 53A; center Black 202A. Immature Under Surface: Near RHS Red 53A and 53B, veins 53A. Mature Upper Surface: Near RHS Red 53A with 46A and 53B; center Black 202A. Mature Under Surface: Near RHS Red 53B and 46B, veins 53A. Aging Upper Surface: Near RHS Purple-Red 60A with 59A and 59B; center Black 202A. Aging Under Surface: Near RHS Purple-Red 60A and 60B, veins 59A.

Brachts:
- *Texture*.—Pubescent.
- *Color*.—Upper Surface: RHS Green NN137A. Under Surface: RHS Green 137C.

Peduncle:
- *Length*.—48 cm.
- *Diameter*.—1.2 cm.
- *Texture*.—Pubescent.
- *Strength*.—Strong.
- *Color*.—RHS Yellow-Green 144C and 144D.

REPRODUCTIVE ORGANS

Gynoecium:
- *Pistil length*.—2 cm.
- *Pistil quantity*.—About 13.
- *Pistil color*.—RHS Red N187A, with a hint of 187A.
- *Stigma shape*.—Narrowly oblong.
- *Stigma color*.—RHS Red N187A.
- *Ovary color*.—RHS Green 138A.

Androecium:
- *Stamens quantity*.—300 to 350.
- *Stamens length*.—3.2 cm.
- *Filament length*.—2.9 cm.
- *Filament color*.—RHS Red 187B, with White NN155D.

*Anther length*.—3 mm.
*Anther shape*.—Narrowly oblong, basifixed.
*Anther color*.—RHS Red N187A.
*Pollen quantity*.—Low.
*Pollen color*.—Near RHS Red N187A.

OTHER CHARACTERISTICS

Fruit:
*Quantity*.—1 per flower.
*Type*.—Capsule.
*Length*.—2.2 cm.
*Diameter*.—2.7 cm.
*Color*.—RHS Green 137A.

Seeds:
*Quantity*.—800 to 900.
*Length*.—1 mm.
*Diameter*.—1 mm.
*Color*.—RHS Black 202A-B.

Disease resistance: Higher tolerance to *Botrytis* than other *Papaver* cultivars.

Drought tolerance and cold tolerance: Not observed to date.

What is claimed is:

1. A new and distinct cultivar of *Papaver* plant named 'HG01' as herein illustrated and described.

* * * * *